United States Patent [19]

Tanida et al.

[11] Patent Number: 5,118,836
[45] Date of Patent: Jun. 2, 1992

[54] OPTICALLY ACTIVE FLUORINE-CONTAINING 3-HYDROXYBUTYRIC ACID ESTERS AND PROCESS FOR PRODUCING THE SAME

[75] Inventors: Kaichi Tanida, Osaka; Yoshiichi Suzuki, Tokyo, both of Japan

[73] Assignee: Showa Shell Sekiyu Kabushiki Kaisha, Tokyo, Japan

[21] Appl. No.: 610,748

[22] Filed: Nov. 8, 1990

[30] Foreign Application Priority Data

Nov. 8, 1989 [JP] Japan .................. 1-290346

[51] Int. Cl.$^5$ .............................. C07C 64/66
[52] U.S. Cl. ..................................... 560/184
[58] Field of Search ........................... 560/184

[56] References Cited

PUBLICATIONS

Chemical abstracts 111:31747P (Jul. 24, 1989) No. 4 p. 621.
Chemical abstracts 112:6144C (Jan. 1, 1990) No. 1 p. 561.
Regeants for Organic Synthesis 8: 427 (1980).
Lin, et al., "A Microbially Based Approach for the Preparation of Chiral Molecules Possessing the Trifluoromethyl Group", J. Org. Chem. 1987, 52, 3211–3217.
Mori, et al., "Synthesis of Three Stereoisomeric Forms of 2-8, Dimethyl-1,7 Dioxaspiro[5.5] Undecane, the Main Component of the Cephalic Secretion of Andrena Wilkella", Tetrahedron vol. 37, No. 18, pp. 3221–3225, 1981.
Kitazume, et al., "Enzymatic Syntheses of Chiral Building Blocks With Trifluoromethyl Or Pentafluoroethyl Groups", Journal of Fluorine Chemistry, 29 (1985) 431–444.
New Syntheses of Physiologically Active Compounds Using the Chiral Synthons Produced by Microbial or Enzymatic Reactions—Journal of Synthetic Organic Chemistry, Japan 331 (Apr. 1987).

*Primary Examiner*—Bruce Gray
*Attorney, Agent, or Firm*—Cushman, Darby & Cushman

[57] ABSTRACT

An optically active (3R)- or (3S)-fluorine-containing-3-hydroxybutyric acid ester represented by the formula:

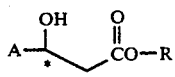

wherein R represents an alkyl group of $C_3$-$C_{16}$ and A represents $CF_3$, $CHF_2$ or $CH_2F$, which is useful for synthesis of optically active substances, is prepared with high optical purity by ester exchange reaction between an alcohol represented by the formula:

ROH wherein R is as defined above and optically active (3R)- or (3S)-fluorine-containing-3-hydroxybutyric acid ethyl ester of

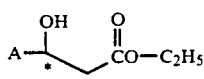

in the presence of an ammonium salt of sulfonic acid.

12 Claims, No Drawings

OPTICALLY ACTIVE FLUORINE-CONTAINING 3-HYDROXYBUTYRIC ACID ESTERS AND PROCESS FOR PRODUCING THE SAME

The present invention relates to optically active (3R)- or (3S)-fluorine-containing-3-hydroxybutyric acid esters and a process for producing the esters in high optical purity. Optically active β-hydroxy acids including the present compounds are bifunctional compounds and useful for synthesis of various optically active substances. For instance, optically active β-hydroxyisobutyric acid is used for synthesis of captopril, a hypotensive agent, or (R)-3-dimethylamino-2-methylpropyl chloride, an intermediate for levomepromazine, tranquilizer. Optically active substances having a fluoromethyl group and reactivity are prepared from the present compounds.

Compounds represented by the formula (I):

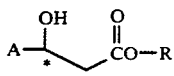
(I)

(wherein R represents an alkyl group of $C_3$–$C_{16}$ and A represents $CF_3$, $CHF_2$ or $CH_2F$) have been synthesized by synthesizing respective precursors, for example, when R in compound (I) is an alkyl group of C=9, the starting material having an alkyl group of C=9 is synthesized and then subjecting the precursors to asymmetric reduction or asymmetric hydrolysis. However, in this case, starting materials corresponding to respective desired derivatives must be prepared and besides, objective compounds of high optical purity is not obtained. If various esters are obtained from one starting material, efficiency is very high. The best way for this purpose is to carry out ester exchange reaction using a starting material of high optical purity.

Under the circumstances, the inventors have carried out ester exchange reaction of an optically active (3R) or (3S)-fluorine-containing -3-hydroxybutyric acid ethyl ester represented by the formula (III):

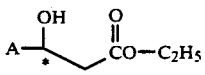
(III)

This ester exchange reaction includes the following process which is according to known ester exchange reaction.

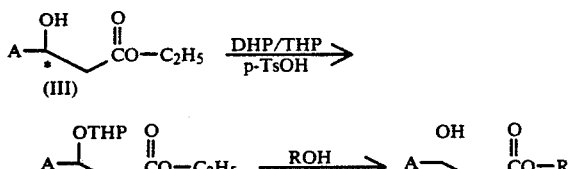

: Racemic modification
DHP: Dihydropyran
THP: Tetrahydropyran
p-TsOH: p-toluenesulfonic acid —OTHP in the reaction formula: This means that OH group of the formula (III) is allowed to react with tetrahydropyran (THP) to protect OH group as —OTHP group.

However, the desired optically active fluorine-containing-3-hydroxybutyric esters are not obtained by the above process, but only racemic modification free from protecting group is obtained. This is considered that, due to strong electron-attracting effect of fluorine-containing methyl group such as trifluoromethyl group, optically active substance as shown by the formula (I) is not obtained.

The present invention provides a novel optically active (3R) or (3S)-fluorine-containing-3-hydroxybutyric acid ester represented by the formula (I) and a novel process for producing the ester in a high optical purity.

One of the present invention relates to an optically active (3R) or (3S)-fluorine-containing-3-hydroxybutyric acid ester represented by the formula (I):

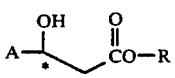
(I)

(wherein R represents an alkyl group of $C_3$–$C_{16}$ and A represents $CF_3$, $CHF_2$ or $CH_2F$).

The present invention also relates to a process for production of the above compound (I) and is characterized by carrying out ester exchange reaction of an alcohol represented by the formula (II): and an optically active (3R) or (3S)-fluorine-containing-3-hydroxybutyric acid ethyl ester represented by the formula (II):

ROH (II)

(wherein R is the same as defined above)

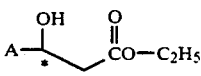
(III)

(wherein A is the same as defined above) in the presence of a catalyst of an ammonium salt of a sulfonic acid derivative represented by the formula (IV):

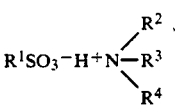
(IV)

(wherein $R^1$ represents a group selected from the group consisting of lower alkyl group and substituted or unsubstituted phenyl group and $R^2$, $R^3$ and $R^4$ each represents lower alkyl group which may be identical or different or form a pyridinium group together with N).

The starting material ethyl (3R)-4,4,4-trifluoro-3-hydroxybutyrate, one of the compounds (III), is produced by known processes, for example, asymmetric reduction reaction of acetoacetic acid esters with baker's yeast ["Tetrahedron", Vol. 37, No. 18, Page 3221 (1981), "J. Fluro. Chem.", Vol. 29, Page 431 (1984)] and asymmetric hydrolysis reaction of acetoacetic acid ester with lipase ["J. Org. Chem.", Vol. 52, page 3211 (1987)]. When the $CF_3$ group is $CHF_2$ group or replaced by a $CH_2F$ group, the desired product is also produced in accordance with the above processes.

The above reaction is preferably carried out in a suitable solvent. Examples of the solvent include aromatic hydrocarbon solvents such as benzene, toluene, and xylene, ether solvents such as ether and tetrahydrofuran, and hydrocarbon solvents such as hexane and heptane. Among them preferred are aromatic hydrocarbon solvents such as benzene, toluene and xylene.

Ammonium salts (IV) include, for example, tertiary ammonium salts such as pyridinium methanesulfonate, pyridinium benzenesulfonate, pyridium toluenesulfonate, trimethylammonium benzenesulfonate, trimethylammonium toluenesulfonate, and trimethylammonium methanesulfonate. But pyridinium toluenesulfonate is preferred for synthetic purpose. The salts are used in an amount of 0.1–1.0 mol based on the ethyl ester.

Reaction temperature is preferably within the range of 80°–150° C. and especially, amount of toluene is adjusted so that 110°–125° C. is maintained. Progress of reaction is confirmed each time by GC analysis (column PEG20M 200° C.) and the reaction is terminated at the time when peak of the starting material disappears. Reaction time is maintained for 8–15 hours. On completion of the reaction, the reaction product is cooled and diluted with water. Optical purity of the ester is determined by converting it to (R)-(+)-α-methoxy-α-trifluoromethylphenylacetic acid ester and then separating diastereomer by GC analysis (Analysis column: Methyl-Si 0.25 φmm ×60 m 50° C.–250° C.). The optical purity of the resulting ester is nearly the same as that of the starting ethyl ester. This shows that no epimer is produced by this reaction. It is very surprising that the objective esters is produced with such high optical purity.

The present invention will be explained in detail by the following reference example and working examples.

REFERENCE EXAMPLE

Preparation of ethyl (3R)-(+)-4,4,4-trifluoro-3-hydroxybutyrate

Sugar (300 g) and water (1,000 g) were charged in a two liter four-necked flask and were stirred until sugar was completely dissolved. Dry yeast (Oriental Yeast Co.) (100 g) was added thereto and spinner culturing was conducted for 15 minutes keeping the inner temperature at 30°–33° C. Thereto was added ethyl 4,4,4-trifluoroacetoacetate (20 g), followed by stirring at the same temperature for 5 hours. After termination of reaction, toluene (500 ml) was added to stop the reaction. Insoluble matters were removed from the reaction mixture by Celite filtration and then the filtrate was separated in two layers. Toluene layer was washed with 10% aqueous sodium chloride solution and then toluene was distilled off under reduced pressure to obtain 19 g of an oily residue. This residue was rectified by Widmer distiller to obtain 12 g (yield 60%) of an oily product as a fraction of boiling 50°–51° C./4 mmHg.

GC analysis: 99.4 % (column PEG 20M 170° C. constant $[\alpha]_D^{30} = +12.5°$ (c=1.25 CHCl_3)

$\alpha_D^{30} = +16.2°$ (neat)

Optical purity thereof as (R)-(+)-MTPA ester was determined to be 93% ee by GC analysis (column Methyl-Si 0.25 φmm ×60 m 50° C.-250° C.)

(Note) ee: enantiomeric excess

Method of indication of optical purity in % which shows optically active enantiomers (R) and (S).

$$\% \text{ ee} = \frac{[R] - [S]}{[R] + [S]} \times 100$$

In above formula, when [R] is present in larger amount than [S].

EXAMPLE 1

Preparation of butyl (3R)-(+)-4,4,4-trifluoro-3-hydroxybutyrate

Ethyl (3R)-(+)-4,4,4-trifluoro-3-hydroxybutyrate (5.0 g), n-butanol (25 ml), pyridium toluenesulfonate (5.0 g) and toluene (25 ml) were charged in a 100 ml four-necked flask equipped with a stirrer, a thermometer and a condenser and stirred. Refluxing under heating at 110° C. was carried out for 3 hours and then solvent was removed over a period of 1 hour by elevating the inner temperature to 120° C. Further, toluene (20 ml) and n-butanol (20 ml) were added, followed by continuing refluxing under heating for 3 hours. Solvent was again removed over a period of 1 hour by elevating the inner temperature to 120° C. After disappearance of ethyl ester was confirmed by GC analysis, the product was diluted with toluene (50 ml) and washed with water. Toluene was distilled off under reduced pressure to obtain 10 g of a crude oily product. This crude oily product was rectified by Widmer distiller to obtain 4.0 g (yield 73 %) of an oily product as a fraction of a boiling point of 68°–69° C./3 mmHg.

GC analysis: 99.0 % (column PEG20M 170° C. constant)

IR (liquid film): 3460, 2960, 2940, 2880, 1730, 1280, 1175, 1135, 665 cm$^{-1}$

NMR (CDCl_3 δTMS internal standard):
0.90 (3H t J=6.0 Hz) 1.30–1.90 (4H m),
2.85 (2H d J=6.0HHz) 3.85(1H-OH),
4.15 (2H t J=6.0 Hz),
4.40 (1H q J=6.0 Hz)ppm
$[\alpha]_D^{30} = +9.02°$ (c=1.84 CHCl_3)

Optical purity as (R)-(+)-MTPA ester was determined to be 92% ee by GC analysis (column Methyl-Si 0.25 φmm ×60 m 50° C.-250° C.) in accordance with conventional method.

EXAMPLE 2

Preparation of octyl (3R)-(+)-4,4,4-trifluoro-3-hydroxybutyrate

Ethyl (3R)-(+)-4,4,4-trifluoro-3-hydroxybutyrate (5.0 g), n-octanol (25 ml), pyridium toluenesulfonate (5.0 g) and toluene (50 ml) were charged in a 100 ml four-necked flask equipped with a stirrer, a thermometer and a condenser and stirred. Refluxing under heating was carried out at 120° C. for 5 hours and then solvent was removed over a period of 1 hour by elevating the inner temperature to 130° C. Further, toluene (50 ml) was added, followed by refluxing under heating at 120° C. After disappearance of the starting ethyl ester was confirmed by GC analysis, the product was cooled and washed with water and toluene layer was separated. Toluene was distilled off under reduced pressure to obtain 40.0 g of a crude oily product. This oily product was rectified by Widmer distiller to remove excess n-octanol. Then, the product was again rectified to obtain 6.0 g (yield 85%) of an oily product as a fraction of a boiling point of 101°–102° C./3 mmHg. GC analysis: 99.1 % (column PEG20M 200° C. constant)

IR (liquid film: 3450, 2960, 2920, 2850, 1725, 1280, 1170, 1130, 660 cm$^{-1}$

NMR (CDCl_3δTMS internal standard: 0.90 (3H t) 1.10–1.80 (12H m), 2.35 (1H -OH) 2.72 (2H d J=6.0Hz), 4.28 (2H t J=6.0Hz), 4.45 (1H q J=6.0Hz)ppm
[α]$_D^{30}$=+7.26° (c=1.20 CHCl$_3$)

In accordance with conventional method, optical purity as (R)-(+)-MTPA ester was determined to be 92.5 % ee by GC analysis (column Methyl-Si 0.25 φmm ×60 m 50° C.-250° C.)

EXAMPLE 3

Preparation of hexyl (3R)-(+)-4,4,4-trifluoro-hydroxybutyrate

In the same manner as in Example 2, hexyl (3R)-(+)-4,4,4-trifluoro-3-hydroxybutyrate was obtained as an oily product in a yield of 72 %. Boiling point: 78°-80° C./3 mmHg.

IR (liquid film): 3460, 2970, 2945, 2865, 1730, 1285, 1175, 1135, 665, cm$^{-1}$ NMR (CDCl$_3$ δTMS internal standard): 0.90 (3H t) 1.10-1.80 (8H m), 2.65 (2H d J=6.0Hz) 4.05 (1H -OH), 4.12 (2H t J=6.0Hz), 4.45 (1H q J=6.0Hz)ppm
[α]$_D^{30}$=+7.79° (c=1.24 CHCl$_3$)
Optical purity 93.0% ee

EXAMPLE 4

Preparation of heptyl (3R)-(+)-4,4,4-trifluoro-3-hydroxybutyrate

In the same manner as in Example 2, heptyl (3R)-(+)-4,4,4-trifluoro-3-hydroxybutyrate was obtained as an oily product in a yield of 75%. Boiling point: 89°-90° C./3 mmHg.

IR (liquid film): 3430, 2955, 2945, 2860, 1730, 1310, 1280, 1175, 1140, 650 cm$^{-1}$ NMR (CDCl$_3$ δMS internal standard):
0.90 (3H t) 1.10-1.80 (10H m),
2.75 (2H d J=6.0Hz) 4.00 (1H -OH),
4.15 (2H t J=6.0Hz),
4.45 (1H q J=6.0Hz)ppm
[α]$_D^{30}$=+7.38° (c=1.66 CHCl$_3$)
Optical purity 92.0 % ee The compounds of the present invention are useful as organic functional material, liquid crystal compound and optical element and intermediate for pharmaceutical and agricultural chemicals.

According to the present process, various optically active fluorine-containing-3-hydroxybutyric acid ester is easily produced in high optical purity from only one ethyl ester which is inexpensive and easily available as starting material.

We claim:

1. A process for producing an optically active (3R) or (3S)-fluorine-containing-3-hydroxybutyric acid ester represented by the formula (I):

wherein R is a C$_3$-C$_{16}$ alkyl group and A is CF$_3$, CHF$_2$ or CH$_2$F, which comprises carrying out an ester exchange reaction of an alcohol represented by the formula (II):

ROH　(II)

wherein R is as defined above nd optically active (3R) or 3S)-fluorine-containing-3-hydroxybutyric acid ethyl ester represented by the formula (III);

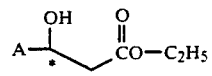

wherein A is as defined above, in the presence of an ammonium salt of sulfonic acid derivative represented by the formula (IV):

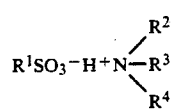

wherein R$^1$ represents a group selected from the group consisting of a lower alkyl group and unsubstituted phenyl group and R$^2$, R$^3$ and R$^4$ represent lower alkyl groups which may be identical or different or form a pyridinium group together with N, as a catalyst.

2. A process according to claim 1, wherein the reaction is carried out in a solvent.

3. A process according to claim 2, wherein the solvent is an aromatic hydrocarbon solvent.

4. A process according to claim 1, wherein amount of the catalyst is 0.1-1.0 mol based on 1 mol of the ethyl ester.

5. A process according to claim 3, wherein reaction temperature is 80°-150° C. and reaction period is 8-15 hours.

6. A process for producing an optically active (3R) or (3S)-fluorine-containing-3-hydroxybutyric acid ester represented by the formula (I):

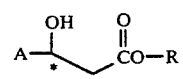

wherein R is a C$_3$-C$_{16}$ alkyl group and A is CF$_3$, CHF$_2$ or CH$_2$F, which comprises carrying out an ester exchange reaction of an alcohol represented by the formula (II):

ROH　(II)

wherein R is as defined above and optically active (3R) or (3S)-fluorine-containing-3-hydroxybutyric acid ethyl ester represented by the formula (III):

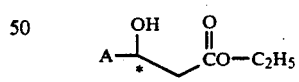

wherein A is as defined above, in the presence of an ammonium salt of sulfonic acid derivative represented by the formula (IV):

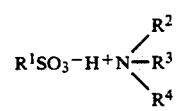

wherein R$^1$ represents a lower-alkyl substituted phenyl group and R$^2$, R$^3$ and R$^4$ represent lower alkyl groups which may be identical or different or form a pyridinium group together with N, as a catalyst.

7. A process according to claim 6, wherein the substituted phenyl group in formula (IV) is

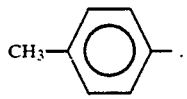

8. A process according to claim 6, wherein the ammonium salt of formula (IV) is pyridinium toluenesulfonate or trimethylammonium toluenesulfonate.

9. A process according to claim 8, wherein A is —CF$_3$.

10. A process according to claim 8, wherein the amount of the catalyst is 0.1–1.0 mol based on 1 mol of the ethyl ester.

11. A process according to claim 8, wherein the reaction temperature is 80°–150° C. and the reaction period is 8–15 hours.

12. A process according to claim 6, wherein the ammonium salt of the sulfonic acid derivative of formula IV is pyridinium toluenesulfonate; said salt is used in an amount of 0.1–1.0 mol based on the ethyl ester; the reaction temperature is maintained from 80° to 150° C.; and the reaction is conducted in a solvent.

* * * * *